US009442063B2

(12) United States Patent
Di et al.

(10) Patent No.: US 9,442,063 B2
(45) Date of Patent: Sep. 13, 2016

(54) MEASUREMENT OF COMPOSITION FOR THIN FILMS

(75) Inventors: Ming Di, Hayward, CA (US); Torsten Kaack, Los Altos, CA (US); Qiang Zhao, Milpitas, CA (US); Xiang Gao, San Jose, CA (US); Leonid Poslavsky, Belmont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 936 days.

(21) Appl. No.: 13/524,053

(22) Filed: Jun. 15, 2012

(65) Prior Publication Data

US 2013/0006539 A1    Jan. 3, 2013

Related U.S. Application Data

(60) Provisional application No. 61/501,635, filed on Jun. 27, 2011.

(51) Int. Cl.
    *G01N 21/21*    (2006.01)
    *G01N 21/84*    (2006.01)

(52) U.S. Cl.
    CPC ......... *G01N 21/211* (2013.01); *G01N 21/8422* (2013.01); *G01N 2021/213* (2013.01)

(58) Field of Classification Search
    CPC ........... G01N 21/211; G01N 21/8422; G01N 2021/213
    See application file for complete search history.

(56) References Cited

U.S. PATENT DOCUMENTS

| | | | |
|---|---|---|---|
| 6,233,046 B1 | 5/2001 | Alba et al. | |
| 7,321,426 B1* | 1/2008 | Poslavsky et al. | 356/369 |
| 7,381,651 B2 | 6/2008 | Sakthivel et al. | |
| 7,821,637 B1* | 10/2010 | Pfeiffer et al. | 356/367 |
| 2003/0058443 A1 | 3/2003 | Xu et al. | |
| 2004/0257567 A1 | 12/2004 | Woollam et al. | |
| 2004/0265477 A1* | 12/2004 | Nabatova-Gabain et al. | . 427/10 |
| 2008/0077352 A1* | 3/2008 | Willis et al. | 702/155 |

OTHER PUBLICATIONS

Brunet-Bruneau et al., Infrared Ellipsometry Investigation of SiOxNy thin films on silicon, Applied Optics, vol. 35, No. 25; Sep. 1, 1996.*
Sancho-Parramon et al., Optical characterization of HfO2 by spectroscopic ellipsometry: dispersion models and direct data inversion, Thin Solid Films (2008).*
Weisstein, Eric W., "Least Squares Fitting." From Mathworld-A Wolfram Web Resource, Available online Mar. 2, 2009.*
Bruzzese, Dominic, Use of Spectroscopic Ellipsometry and Modeling in Determining Composition and Thickness of Barium Strontium Titanate Thin-Films, Drexel University, Jun. 2010.*
Vlad et al., Theoretical and Experimental Study of the Effective Linear and Nonlinear Optical Response of Nano-Structured Silicon, Oct. 11-13, 2010, 2010 International Semiconductor Conference (CAS), vol. 1, pp. 11-18.*
Abstract of Vlad et al. reference, Oct. 11-13, 2010, 2 pp.*
He et al., Structural and Optical Properties of Nitrogen-Incorporated HfO2 Gate Dielectrics Deposited by Reactive Sputtering, 2007, Applied Surface Science 253, pp. 8483-8488.*

* cited by examiner

*Primary Examiner* — Toan Le
(74) *Attorney, Agent, or Firm* — Suiter Swantz pc llo

(57) ABSTRACT

The present invention includes generating a three-dimensional design of experiment (DOE) for a plurality of semiconductor wafers, a first dimension of the DOE being a relative amount of a first component of the thin film, a second dimension of the DOE being a relative amount of a second component of the thin film, a third dimension of the DOE being a thickness of the thin film, acquiring a spectrum for each of the wafers, generating a set of optical dispersion data by extracting a real component (n) and an imaginary component (k) of the complex index of refraction for each of the acquired spectrum, identifying one or more systematic features of the set of optical dispersion data; and generating a multi-component Bruggeman effective medium approximation (BEMA) model utilizing the identified one or more systematic features of the set of optical dispersion data.

33 Claims, 11 Drawing Sheets

| WAFER | THICKNESS | H% (FROM XPS) | N% (FROM XPS) |
|---|---|---|---|
| 7 | 26.28 | 17.43 | 9.72 |
| 8 | 26.90 | 17.09 | 12.97 |
| 9 | 27.37 | 16.83 | 16.45 |
| 10 | 26.19 | 15.12 | 9.77 |
| 11 | 26.48 | 15.15 | 13.73 |
| 12 | 27.27 | 14.72 | 17.45 |
| 13 | 26.00 | 20.12 | 8.96 |
| 14 | 27.02 | 19.57 | 13.23 |
| 15 | 27.33 | 19.11 | 16.20 |

FIG.3

MEASUREMENT OF COMPOSITION FOR THIN FILMS

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled MEASUREMENT OF COMPOSITION FOR HfSiON FILMS, naming Ming Di, Torsten Kaack, Qiang Zhao, Xiang Gao and Leonid Poslaysky as inventors, filed Jun. 27, 2011, Application Ser. No. 61/501,635.

TECHNICAL FIELD

The present invention generally relates to a method and system for measuring the composition of a multi-component thin film deposited on a semiconductor wafer.

BACKGROUND

As demand on specification requirements of semiconductor devices continue to increase, so too will the demand on improved measurement and analysis techniques used to quantify characteristics of semiconductor wafers. In many semiconductor fabrication and processing settings one or more thin films may be deposited onto a semiconductor wafer surface. For instance, thin films may include oxide, nitride, and/or metal layers, among others. Characteristics such as the thickness and composition of each thin film must be tightly controlled during the manufacturing process to ensure proper performance of the resulting semiconductor devices.

Previously, continuous film approximation (CFA) methods have been implemented in order to determine the relative percentage of multiple components of a thin film. For instance, one commonly implemented CFA method includes the Bruggeman effective medium approximation (BEMA). The BEMA model treats a set of components of a given thin film as an alloy. In this regard, the nonlinear BEMA model treats the components of a thin film as though they are mixed perfectly. For example, in the case of HfSiON thin films, a four-component BEMA model may treat Si, $SiO_2$, $HfO_2$, and SiN as four components of the thin film. In turn, the fraction of $HfO_2$ may be correlated to the percentage of hafnium in the film, while the fraction of SiN may be correlated to the nitrogen percentage in the film.

The prior methods consist of a top-down approach, whereby optical dispersion data for the various individual BEMA components (e.g., Si, $SiO_2$, $HfO_2$, and SiN in the case of a 4-component BEMA model for HfSiON) are used to simulate the thin film as a whole. This top-down approach does not provide sufficient detail for the given thin film (e.g., HfSiON). For instance, the prior methods do not provide sufficient measurement performance of the thickness, and relative amount of the components of the film (e.g., Hf percentage or N percentage). As such, it would be desirable to provide a method and system, which cures the deficiencies of the prior art, thereby improving measurement performance (e.g., precision, repeatability, and stability) of the thickness and composition of a given thin film utilizing optical dispersion modeling.

SUMMARY

A method for measuring the composition of a thin of a semiconductor wafer is disclosed. In one aspect, a method may include, but is not limited to, generating a three-dimensional design of experiment (DOE) for a plurality of semiconductor wafers, a first dimension of the DOE being a relative amount of a first component of the thin film, a second dimension of the DOE being a relative amount of a second component of the thin film, a third dimension of the DOE being a thickness of the thin film; acquiring a spectrum for each of the wafers across a selected spectral range; generating a set of optical dispersion data by extracting a real component (n) of a complex index of refraction and an imaginary component (k) of the complex index of refraction across the selected spectral range for each of the acquired spectrum utilizing a regression process applied to a selected dispersion model; identifying one or more systematic features of the set of optical dispersion data; and generating a multi-component Bruggeman effective medium approximation (BEMA) model utilizing the identified one or more systematic features of the set of optical dispersion data and the generated set of optical dispersion data.

In another aspect, the method may include, but is not limited to, generating a three-dimensional design of experiment (DOE) for a plurality of semiconductor wafers, a first dimension of the DOE being a relative amount of a first component of the thin film, a second dimension of the DOE being a relative amount of a second component of the thin film, a third dimension of the DOE being a thickness of the thin film; acquiring a spectrum for each of the wafers across a selected spectral range; generating a set of optical dispersion data by extracting a real component (n) of a complex index of refraction and an imaginary component (k) of the complex index of refraction across the selected spectral range for each of the acquired spectrum utilizing a regression process applied to a selected dispersion model; identifying one or more systematic features of the set of optical dispersion data; and generating a two-dimensional look up model utilizing the identified one or more systematic features of the set of optical dispersion data and the generated set of optical dispersion data.

A system for measuring the composition of a thin film of a semiconductor wafer is disclosed. In one aspect, a system may include, but is not limited to, an illuminator; a spectrometer; one or more computing systems configured to: generate a three-dimensional design of experiment (DOE) for a plurality of semiconductor wafers, a first dimension of the DOE being a relative amount of a first component of the thin film, a second dimension of the DOE being a relative amount of a second component of the thin film, a third dimension of the DOE being a thickness of the thin film; receive a spectrum for each of the wafers across a selected spectral range from the spectrometer; generate a set of optical dispersion data by extracting a real component (n) of a complex index of refraction and an imaginary component (k) of the complex index of refraction across the selected spectral range for each of the received spectrum utilizing a regression process applied to a selected dispersion model; identify one or more systematic features of the set of optical dispersion data; generate a two-dimensional look up model utilizing the identified one or more systematic features of the set of optical dispersion data and the generated set of optical dispersion data; and generate at least one of a two-dimensional look up model or multi-component Bruggeman effective medium approximation (BEMA) model utilizing the identified one or more systematic features of the set of optical dispersion data and the generated set of optical dispersion data.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 3 is a table illustrating a three-by-three two-dimensional design of experiment (DOE), in accordance with an alternative embodiment of the present invention.

DETAILED DESCRIPTION OF THE INVENTION

Reference will now be made in detail to the subject matter disclosed, which is illustrated in the accompanying drawings.

Referring generally to FIGS. 1 through 6, a system and method for measuring the composition of a thin film of a semiconductor wafer is described in accordance with the present disclosure.

As used throughout the present disclosure, the term "wafer" generally refers to a substrate formed of a semiconductor or non-semiconductor material. For example, a semiconductor or non-semiconductor material may include, but is not limited to, monocrystalline silicon, gallium arsenide, and indium phosphide. A wafer may include one or more layers. For instance, such layers may include, but are not limited to, a resist, a dielectric material, a conductive material, and a semiconductive material. Many different types of such layers are known in the art, and the term wafer as used herein is intended to encompass a wafer on which all types of such layers may be formed.

A typical semiconductor process includes wafer processing by lot. As used herein a "lot" is a group of wafers (e.g., group of 25 wafers) which are processed together. Each wafer in the lot is comprised of many exposure fields from the lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Figure 1:
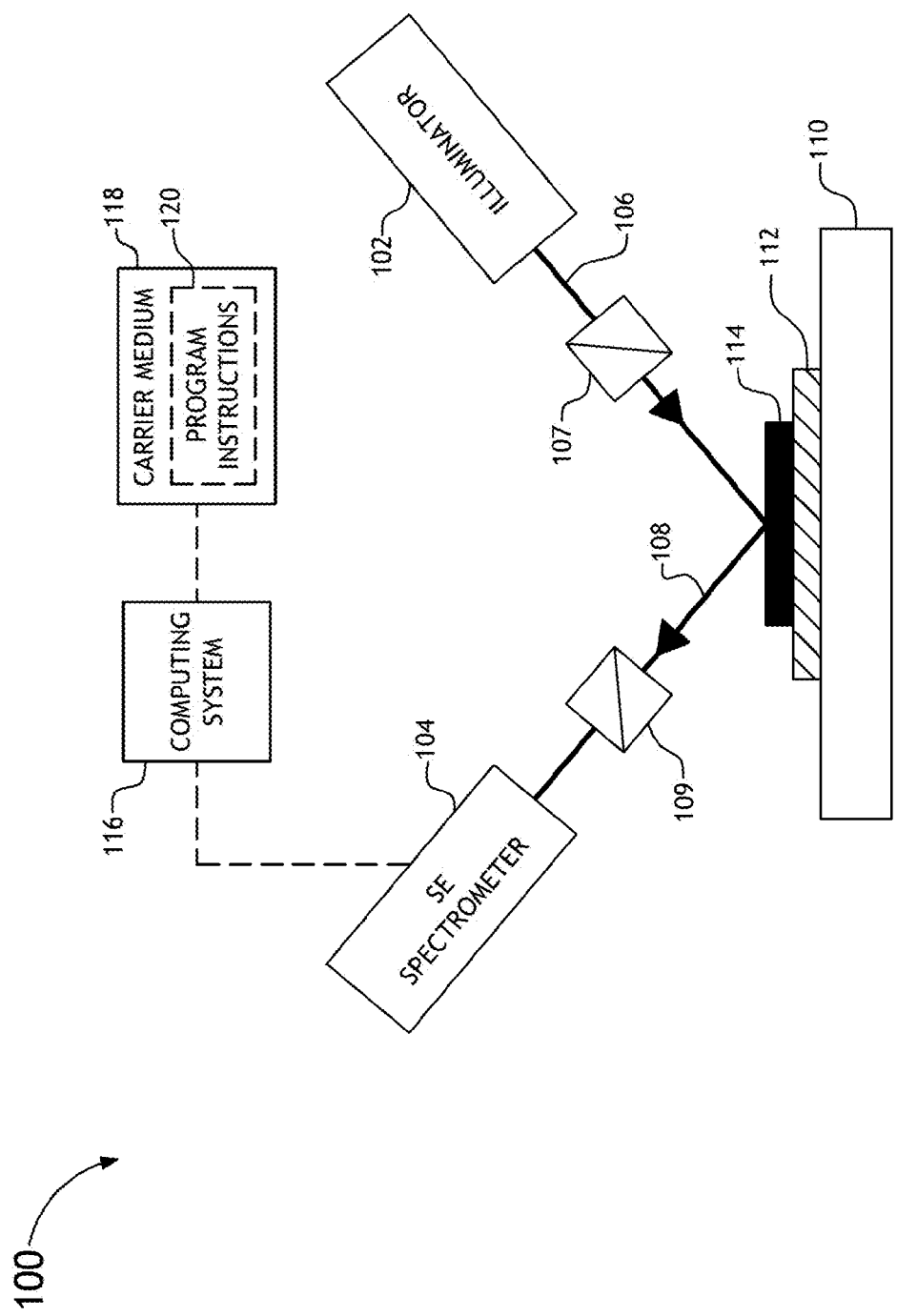
FIG. 1 illustrates a block diagram view of a system for measuring the composition of a thin film of a semiconductor wafer, in accordance with the present invention.

FIG. 1 illustrates a system 100 for measuring the composition of a thin film of a semiconductor wafer, in accordance with one embodiment of the present invention. As shown in FIG. 1, the system 100 may be used to perform spectroscopic ellipsometry on one or more films 114 of a semiconductor wafer 112 disposed on a translation stage 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-850 nm) to the thin film (e.g., HfSiON thin film) disposed on the surface of the semiconductor wafer 112. In turn, the spectrometer 104 is configured to receive illumination reflected from the surface of the semiconductor wafer 112. It is further noted that the light emerging from the illuminator 102 is polarized using polarizer 107 in order to produce a polarized illumination beam 106. The radiation reflected by the thin film 114 disposed on the wafer 112 is passed through an analyzer 109 and to the spectrometer 104. In this regard, the radiation received by the spectrometer 104 in the collection beam 108 is compared to the incident radiation of the illumination beam 106, allowing for spectral analysis of the thin film 114.

In a further embodiment, the system 100 may include one or more computing systems 116. In one aspect, the one or more computing systems may be configured to generate a three-dimensional design of experiment (DOE) for a set of semiconductor wafers. In this regard, one dimension of the DOE may include the percentage of one material component of the thin film (e.g., percentage of nitrogen in the thin film), while a second dimension may include the percentage of a second material component of the thin film (e.g., percentage of hafnium in the thin film). Further, the third dimension of the DOE may include a thickness of the thin film, which may be determined utilizing the ellipsometer of system 100.

In one aspect, the one or more computing systems may be communicatively coupled to the spectrometer 104. In this regard, the one or more computing systems 116 may be configured to receive a set of spectral measurements performed by the spectrometer 104 on one or more wafers of a lot. Upon receiving results of the one or more sampling process from the spectrometer, the one or more computing systems 116 may then calculate a set of optical dispersion data. In this regard, the computing system 116 may extract the real component (n) and the imaginary component (k) of the complex index of refraction of the thin film across the selected spectral range (e.g., 150-850 nm) for each of the acquired spectrum from the spectrometer 104. Further, the computing system 116 may extract the n- and k- curves utilizing a regression process (e.g., ordinary least squares regression) applied to a selected dispersion model. In a preferred embodiment, the selected dispersion model may include a sum model with two Tauc Lorentz components (Sum-TL model). In additional embodiments, the selected dispersion model may include a harmonic oscillator model.

In a further embodiment, the computing system 116 may identify systematic features observable in the set of optical dispersion curves. For example, the computing system 116 may be configured to automatically identify trends within a series of optical dispersion curves (e.g., FIGS. 5A-5F), which will be discussed in greater detail further herein. For instance, the computing system 116 may identify trends in the n- and/or k- dispersion curves as a function of increasing relative amount of either the first material component (e.g., nitrogen) or the second material component (e.g., hafnium). In another example, the computing system 116 may be configured to identify trends within the series of optical dispersion curves using the aid of user input. For instance, the series of optical dispersion curves may be presented to a user on a display (not shown), such as a liquid crystal display. The user may then identify trends in the series of optical dispersion curves by entering information into the computing system 116 using a user interface device (e.g., mouse, keyboard, trackpad, trackball, touch screen, or the like). In this regard, the user may select, or "tag," portions of the optical dispersion curves pertinent to analysis, with which the computing system may then, in turn, perform further or refined analysis. Applicant notes that specifics related to the analysis of optical dispersion curves, as shown in FIGS. 5A-5F will be discussed in greater detail further herein.

In a further embodiment, the one or more computing systems 116 may generate a two-dimensional look up model and a multi-component (e.g., nine component) Bruggeman effective medium approximation (BEMA) model based on the identified systematic features of the optical dispersion curves, along with the original raw generated n- and k- optical dispersion curves.

It should be recognized that the various steps described throughout the present disclosure may be carried out by a single computer system 116 or, alternatively, a multiple computer system 116. Moreover, different subsystems of the system 100, such as the spectroscopic ellipsometer 102, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

In another embodiment, the computer system 116 may be communicatively coupled to the spectrometer 104 or the illuminator subsystem 102 of the ellipsometer 102 in any manner known in the art. For example, the one or more computing systems 116 may be coupled to a computing system of the spectrometer 104 of the ellipsometer 102 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive spectral results via a storage medium (i.e., memory). For instance, the spectral results obtained using a spectrometer of an ellipsometer may be stored in a permanent or semi-permanent memory device. In this regard, the spectral results may be imported from an external system.

Moreover, the computer system 116 may send data to external systems via a transmission medium. Moreover, the computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a storage medium such as a read-only memory, a random access memory, a magnetic or optical disk, or a magnetic tape.

The embodiments of the system 100 illustrated in FIG. 1 may be further configured as described herein. In addition, the system 100 may be configured to perform any other step(s) of any of the method embodiment(s) described herein.

Figure 2:
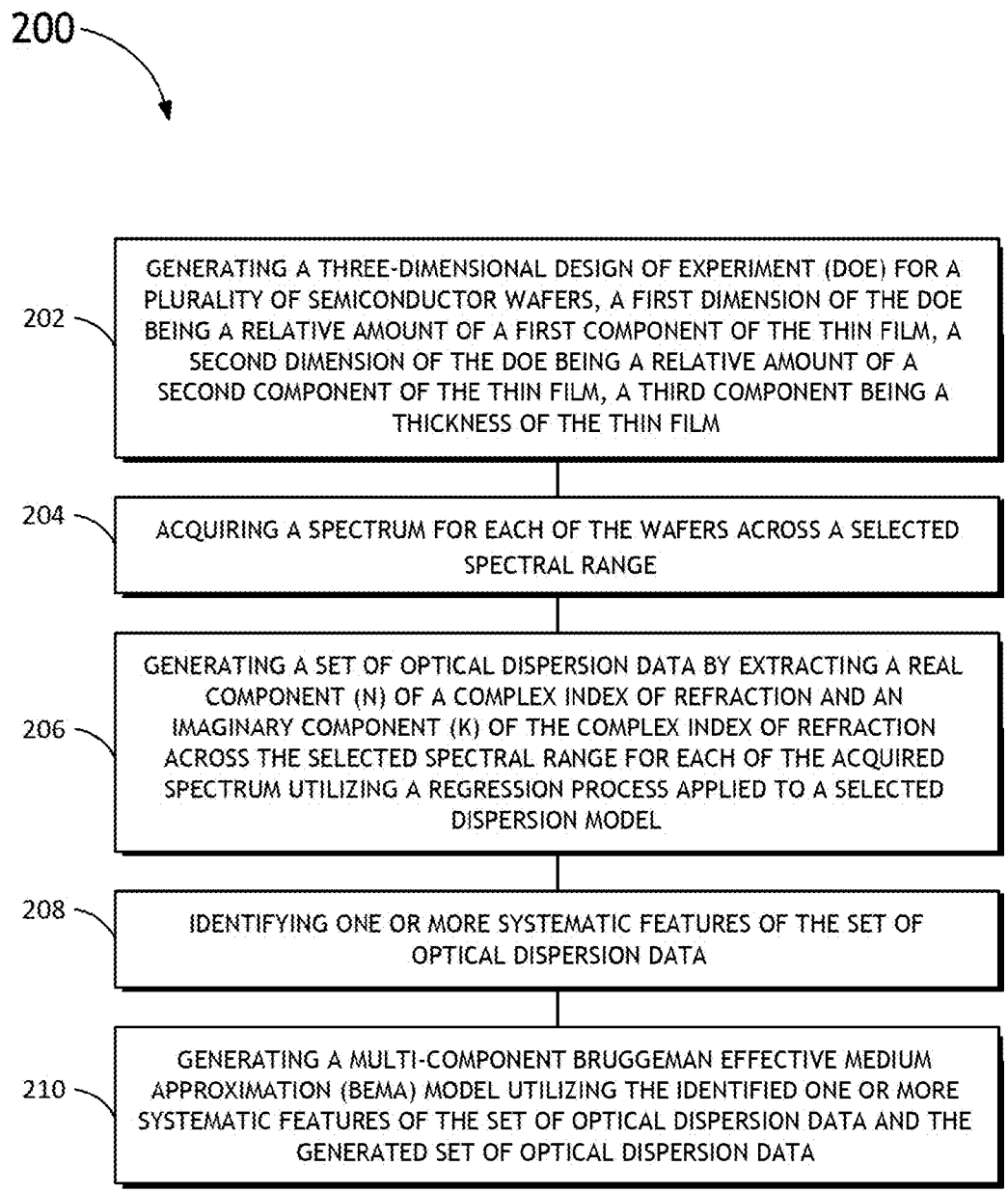
FIG. 2 is a flow diagram illustrating a method for measuring the composition of a thin film of a semiconductor wafer, in accordance with one embodiment of the present invention.

FIG. 2 illustrates a process flow 200 suitable for implementation by the system 100 of the present invention. In one aspect, it is recognized that data processing steps of the process flow 200 may be carried out via a pre-programmed algorithm executed by one or more processors of computing system 116. While the following description is presented in the context of system 100, it is recognized herein that the particular structural aspects of system 100 do not represent limitations and should be interpreted as illustrative only.

In step 202, a three-dimensional design of experiment (DOE) for a plurality of semiconductor wafers may be generated. In one aspect, a first dimension of the DOE consists of the relative amount of a first component (e.g., percentage of nitrogen) of the thin film, while a second dimension of the DOE is the relative amount of a second component (e.g., percentage of hafnium) of the thin film. In another aspect, the third dimension of the DOE includes the thickness of the thin film. For example, the thin film in question may include a multi-element thin film, such as, but not limited to, a HfSiNO thin film. The HfSiNO thin film formed on each of the plurality of wafers of the DOE may be formed by the deposition of Hf and N onto the surface of a silicon wafer. Those skilled in the art will recognize that the presence of a native oxide layer in addition to oxygen content during the deposition of Hf and N both contribute to the oxygen content in the HfSiNO film. It is further recognized herein that the relative amount of the various components of the thin film may be determined by any method known in the art. For example, the relative amounts (i.e., percentages) of hafnium and nitrogen in the multiple HfSiNO films of the DOE may be determined using x-ray photoelectron spectroscopy (XPS).

Figure 4:
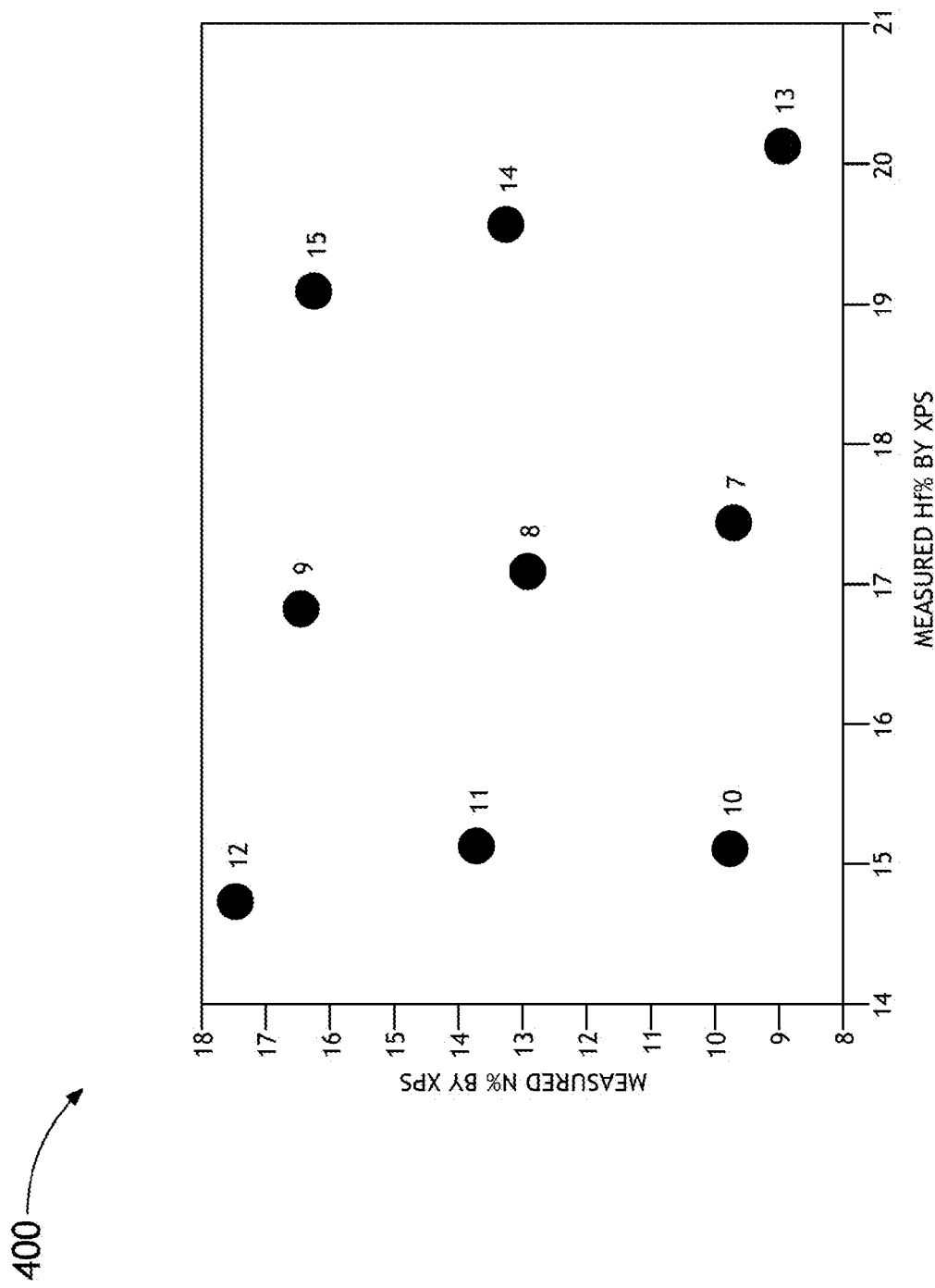
FIG. 4 is a set of data depicting the measured relative nitrogen content and the measured relative hafnium content for each wafer of the DOE, in accordance with one embodiment of the present invention.
Figure 5A:
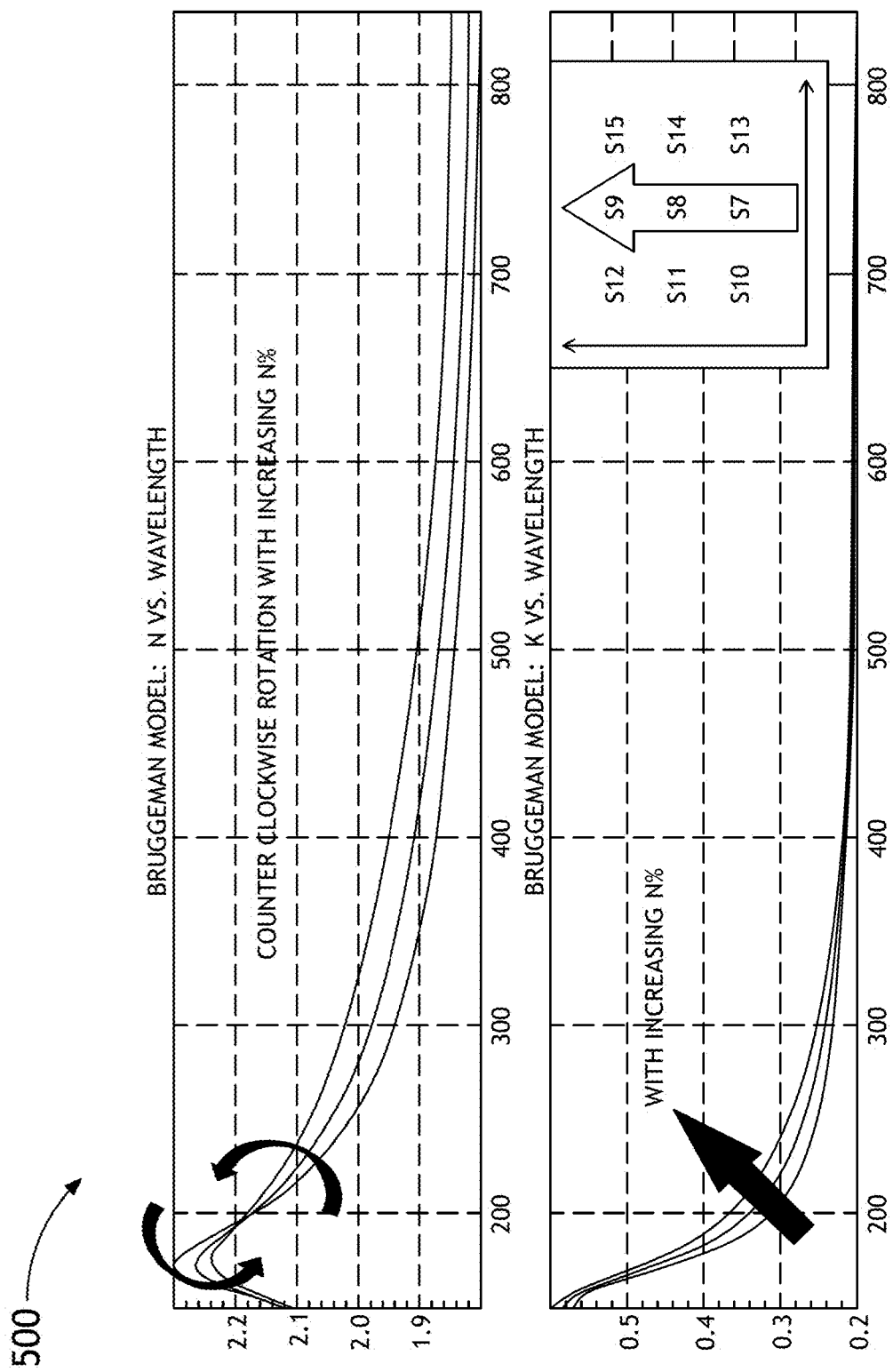
FIGS. 5A-5C depict a series of optical dispersion curves acquired from a portion of the wafers of the DOEs and depicted as a function of increasing nitrogen content, in accordance with one embodiment of the present invention.
Figure 5B:
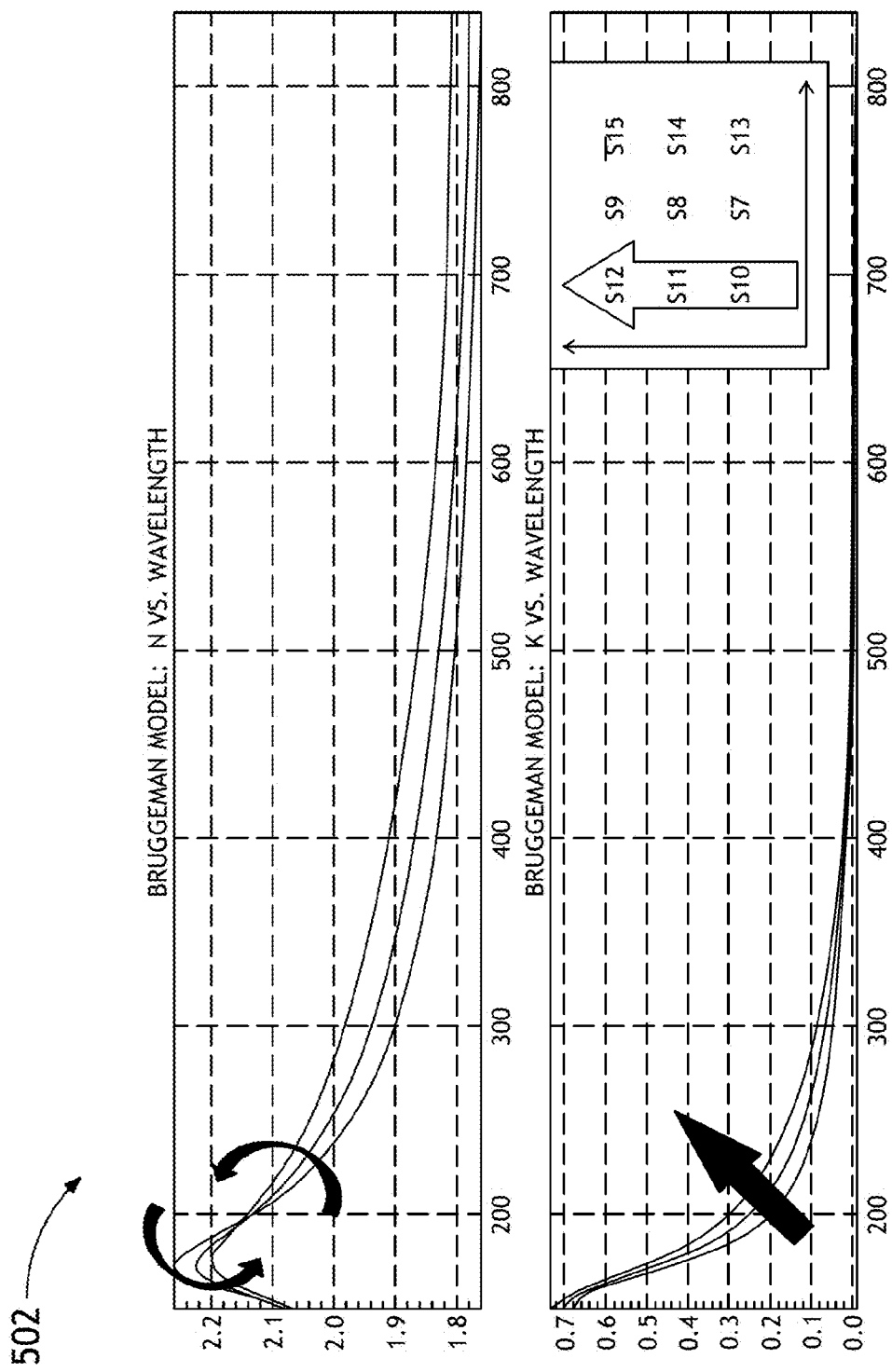
Figure 5C:
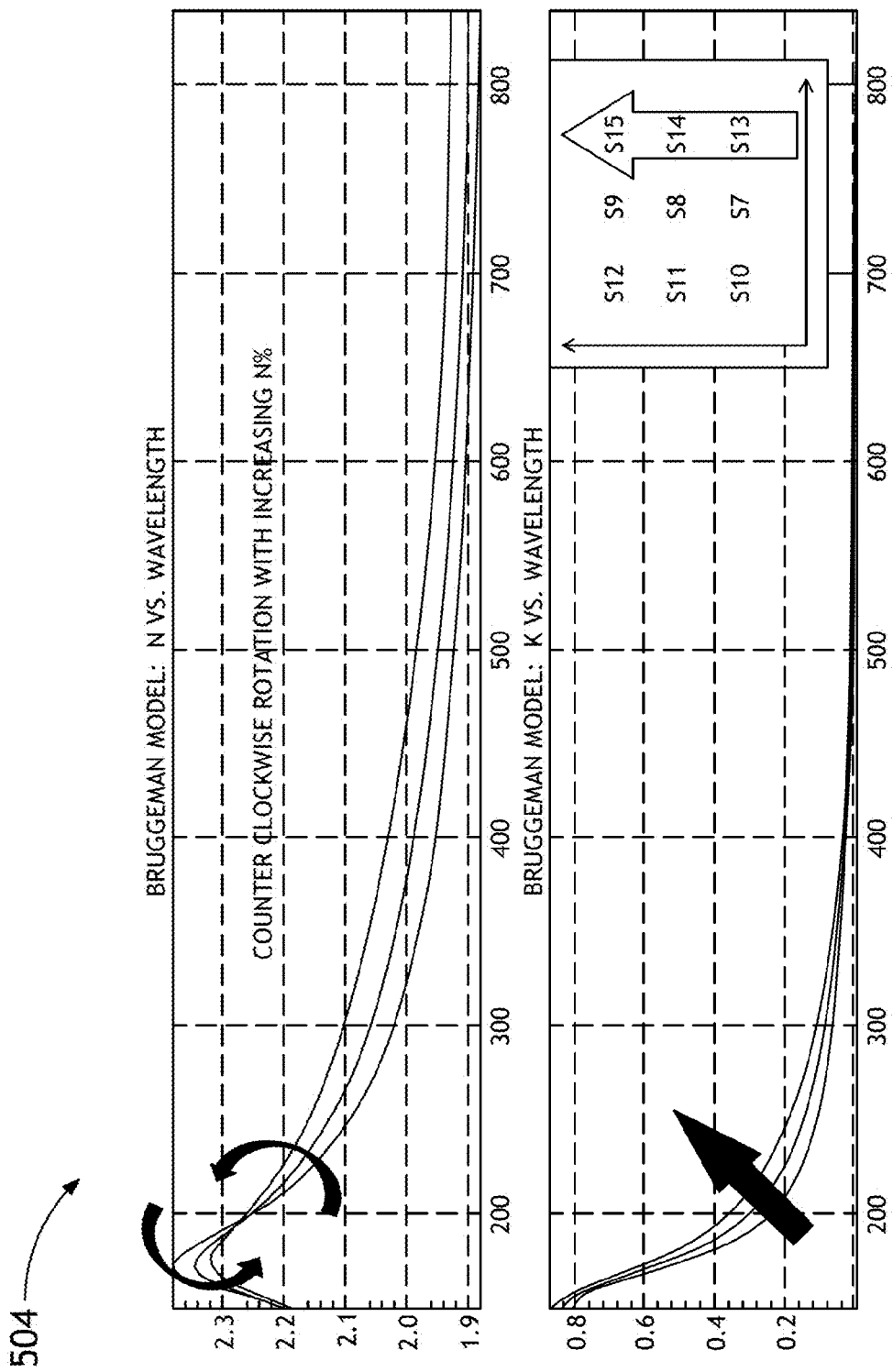
Figure 5D:
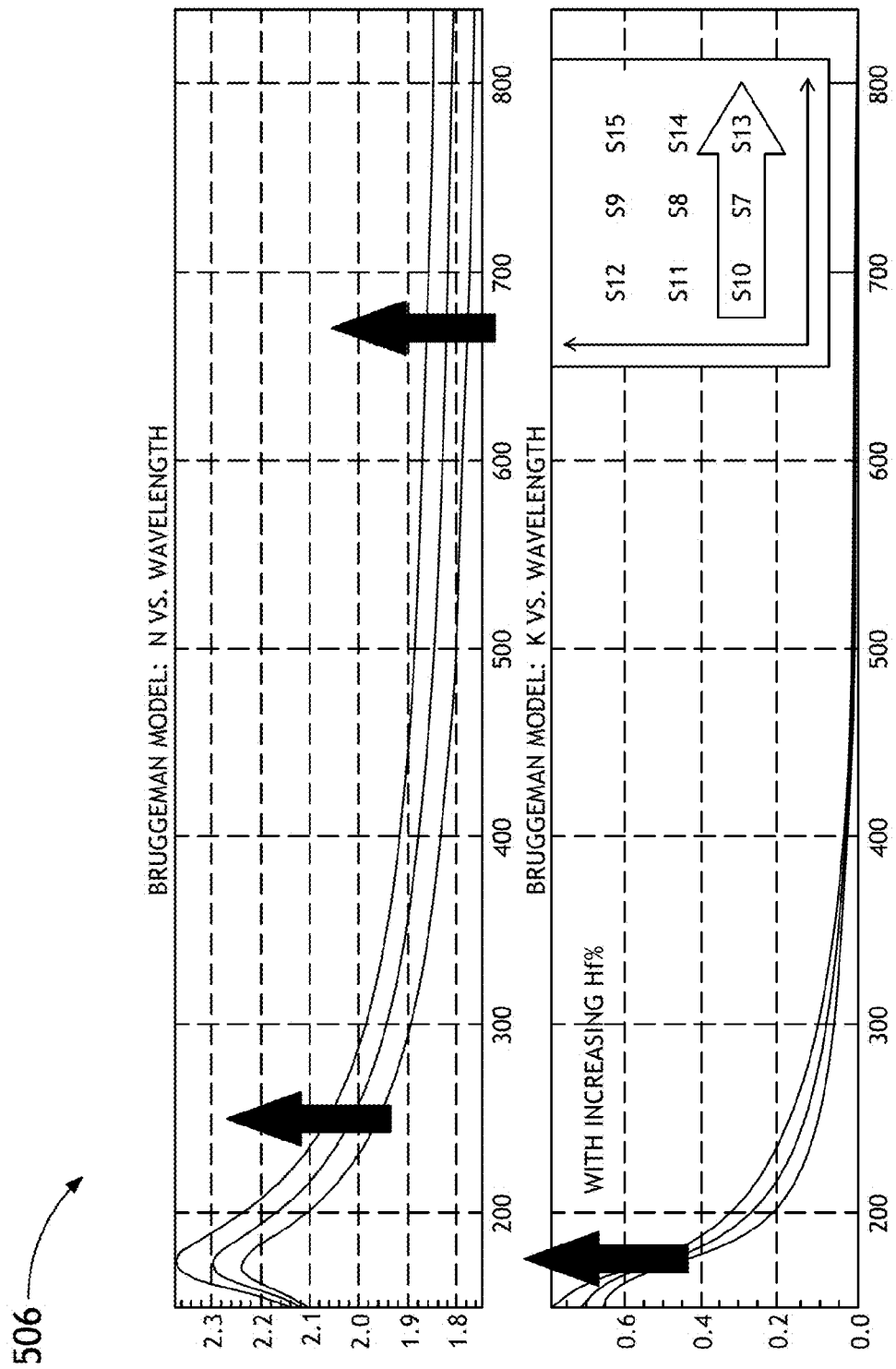
FIGS. 5D-5F depict a series of optical dispersion curves acquired from a portion of the wafers of the DOEs and depicted as a function of increasing hafnium content, in accordance with one embodiment of the present invention.
Figure 5E:
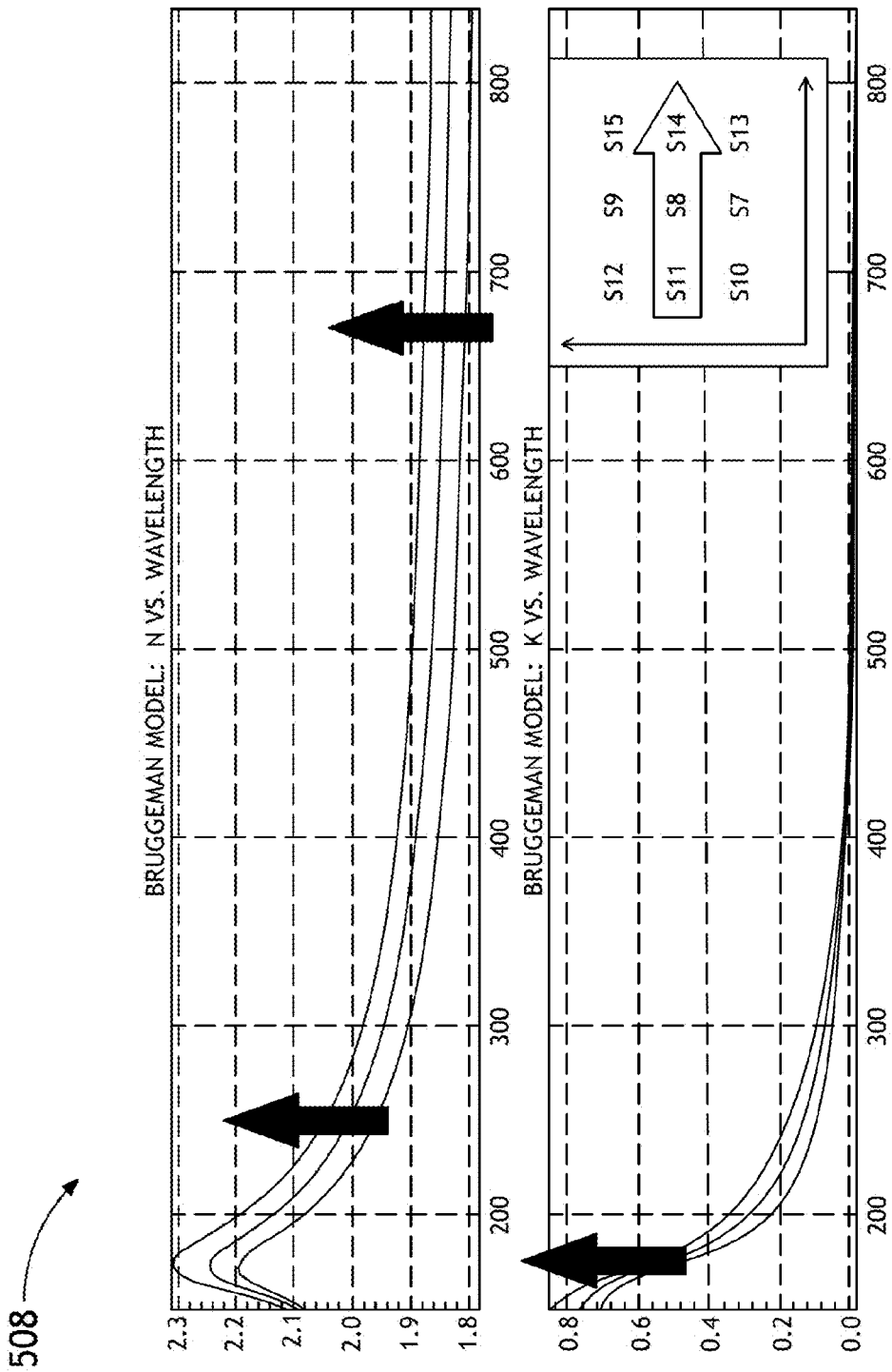
Figure 5F:
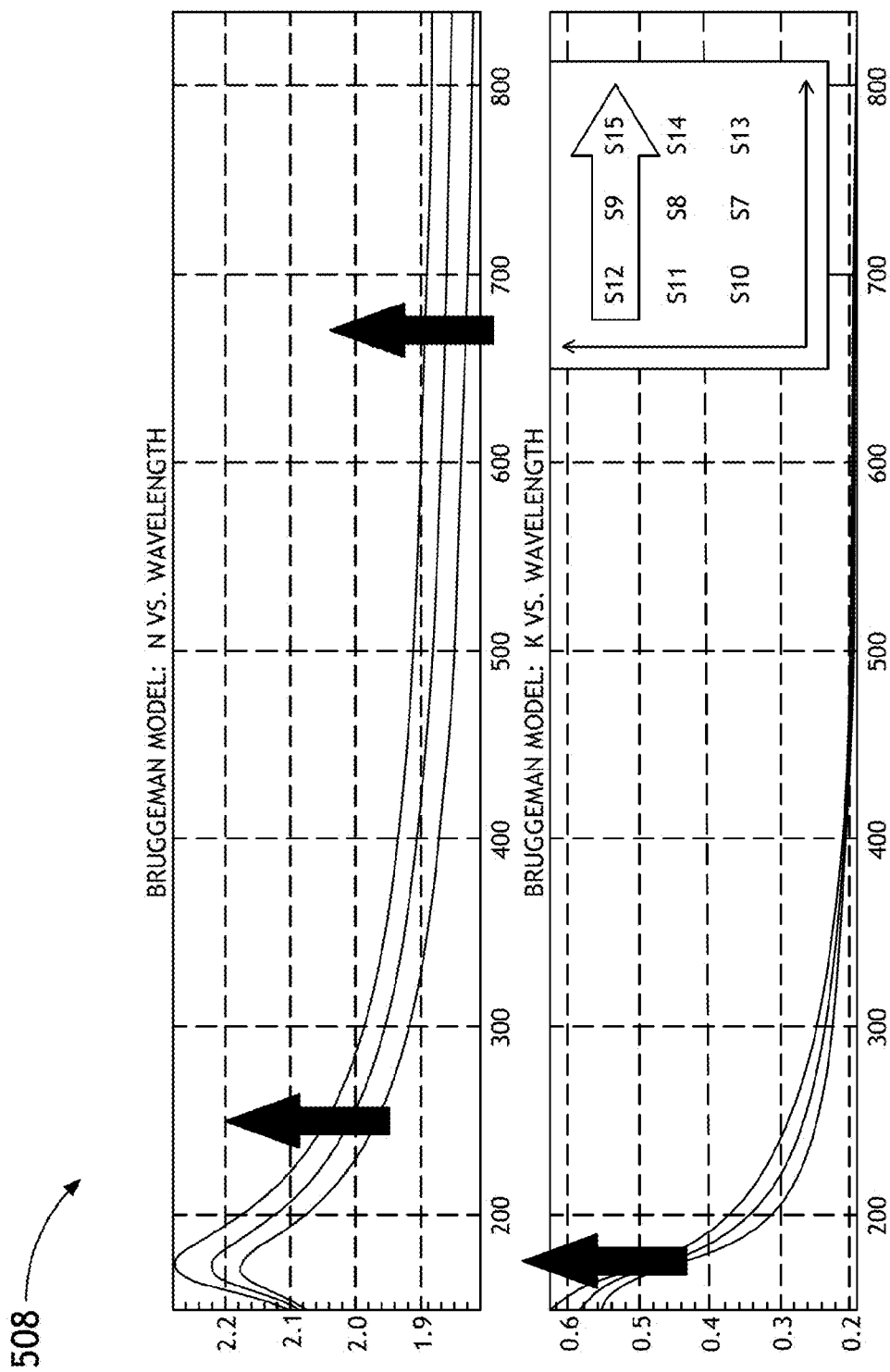

In an additional aspect, it is noted that the DOE for a HfSiNO film includes at least three dimensions. These dimensions include thickness, percentage of hafnium, and percentage of nitrogen. Since thickness of HfSiNO is a parameter that is relatively straightforward to measure, the DOE may be reduced to a two-dimensional DOE by structuring the DOE such that all wafers have approximately the same thickness. FIG. 3 illustrates a table 300 of a 3-by-3 two-dimensional DOE formed for a plurality of wafers, each with a HfSiNO film deposited thereon. In this regard, the reduced two "dimensions" include the variation of the hafnium content and the variation of nitrogen content, with the thickness of each film held relatively constant. The DOE is structured to provide a variation of nitrogen content and hafnium content across the several wafers of the DOE. FIG. 4 illustrates a graph 400 depicting the measured nitrogen context and hafnium content for each of the plurality of wafers of the DOE. Applicant notes that the corresponding wafer number from the DOE depicted in FIG. 3 is illustrated next to each corresponding data point in FIG. 4. As shown in FIG. 4, for each level of nitrogen percentage there exist a number (three in the case of FIG. 4) of hafnium percentage values (moving left to right in FIG. 4), while for each constant hafnium percentage there exist a number (three in the case of FIG. 4) of nitrogen percentage values (moving bottom to top in FIG. 4). In this regard, the fabricated three-by-three two-dimensional DOE is configured to provide a plurality of HfSiNO films with low, medium, and high Hf and N content variations, as shown in FIG. 4.

In step 204, a spectrum may be acquired from the thin films of each of the wafers across a selected spectral range. For example, spectra may be acquired from each of the thin films 114 deposited on the wafers 112 utilizing the spectroscopic ellipsometer 102. For instance, the ellipsometer 102 may include an illuminator 102 and a spectrometer 104, as discussed previously herein. The spectrometer 104 may transmit results associated with a spectroscopic measurement of the thin films of the wafers of the DOE to one or more computing systems 116 for analysis. In another example, the spectra for multiple thin films 114 may be acquired by importing previously obtained spectral data. In this regard, there is no requirement that the spectral acquisition and the subsequent analysis of the spectral data need be contemporaneous or performed in spatial proximity. For instance, spectral data may be stored in memory for analysis at a later time. In another instance, spectral results may be obtained and transmitted to analysis computing system located at a remote location.

In step 206, a set of optical dispersion data may be generated by extracting the real component (n) and the imaginary component (k) of the complex index of refraction across the selected spectral range for each of the acquired spectrum utilizing a regression process applied to a selected dispersion model. In this regard, a regression method may be applied to the measured spectral data using a selected dispersion model. In one embodiment, a sum model with two Tauc-Lorentz components may be utilized to generate the n- and k- dispersion curves for each of the thin films of the wafers. In another embodiment, a single component Tauc-Lorentz may be utilized to generate the n- and k- dispersion curves for each of the thin films of the wafers. In another embodiment, a Cody-Lorentz model may be utilized to generate the n- and k- dispersion curves for each of the thin films of the wafers. In yet another embodiment, a harmonic oscillator model may be utilized to generate the n- and k-dispersion curves for each of the thin films of the wafers.

In step 208, one or more systematic features of the set of optical dispersion data may be identified. FIGS. 5A-5F illustrate a series of optical dispersion curves obtained from six different wafers of a DOE. Each of the FIGS. 5A-5F depict both the real part (n) of the refractive index and the imaginary part (k) of the refractive index as a function of wavelength from 150 to 850 nm. By analyzing the n- and k- dispersion curves of FIGS. 5A-5F the variation in the n- and k- dispersion curves of a function of the increasing amount of a first material component and/or a second material component may be deduced. For example, in FIGS. 5A-5F, an increasing amount of nitrogen in a thin film leads to a counter-clockwise rotation in the n-dispersion curve. This is observed clearly in FIGS. 5A-5C, which depict n as a function of wavelength for increasing nitrogen content. The rotation of the n-dispersion curves is observed at approximately 200 nm. In a general sense, a rotation parameter may be defined as the difference in refractive index between at two separate wavelengths. For example, the rotation parameter associated with the N vs. wavelength data of FIG. 5A may be defined as the difference in the refractive index at 180 nm and 300 nm. It is further noted that the k-dispersion curves increase systematically as a function of increasing relative nitrogen content, as observed in FIGS. 5A through 5C. An additional systematic variation includes the increase of both the n- and k- curves as a function of increasing relative hafnium content, as observed in FIGS. 5D-5F.

In step 210, a multi-component Bruggeman effective medium approximation (BEMA) model may be generated utilizing the identified one or more systematic features of the set of optical dispersion data and the generated set of optical dispersion data. In a general sense, the components of the multi-component model may be used to correlate compounds formed in the thin film (e.g., $HfO_2$ or SiN) with the percentage of another component of the film (e.g., Hf or N). In a further embodiment, the rotation parameter extracted from the refractive index data (as described in step 208) may be used by the multi-component BEMA model to determine the percentage of a component (e.g., nitrogen) in the analyzed film. For instance, the rotation parameters extracted from the data of FIGS. 5A-5C may be utilized to determine the percentage of nitrogen in an analyzed HfSiON film. In one embodiment, the multi-component BEMA model may include a nine-component BEMA model. In other embodiments, the multi-component BEMA model may include a four-, five-, or eight-component BEMA model.

Figure 6:
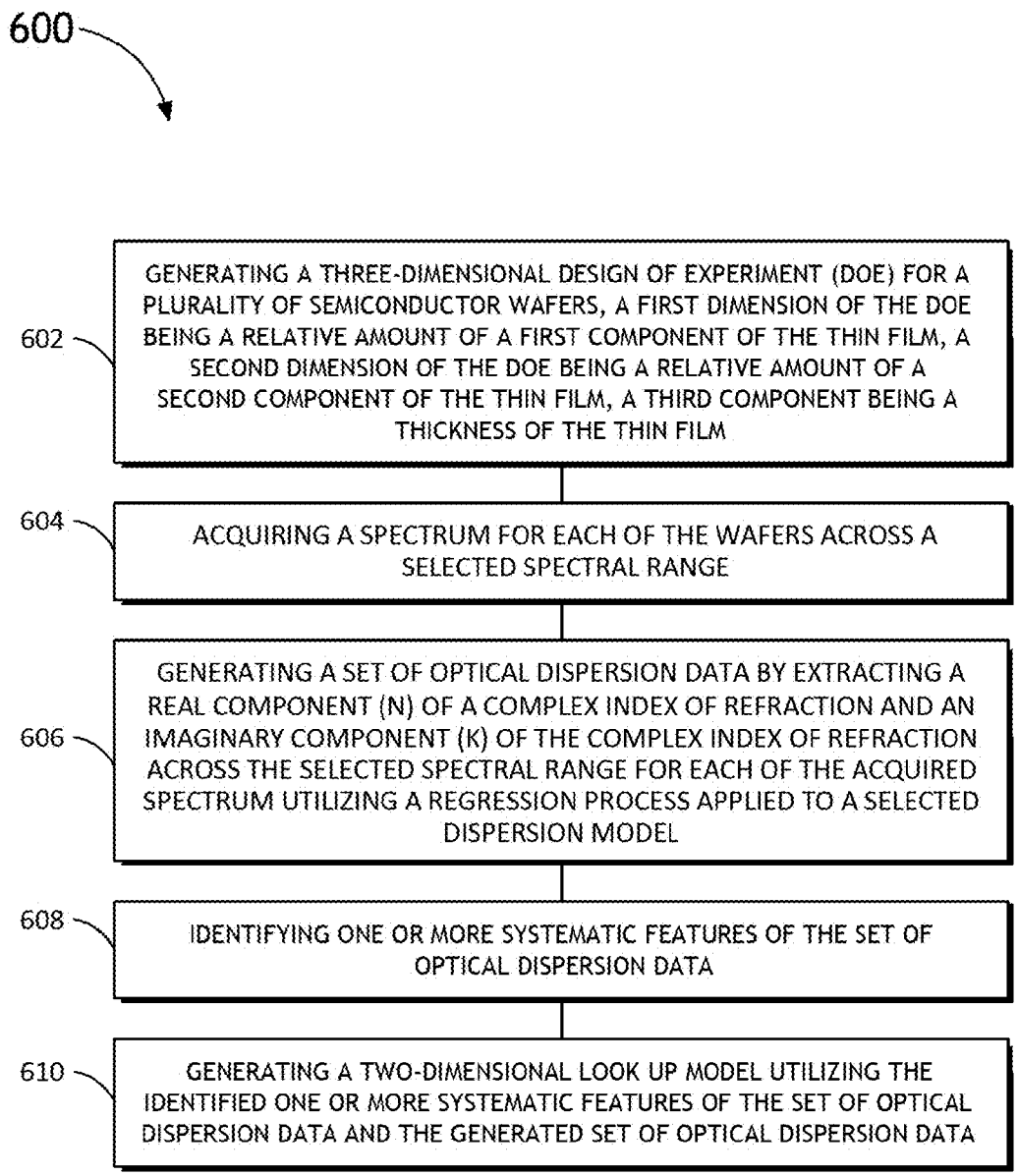
FIG. 6 illustrates a process flow depicting a method of measuring a composition of a thin film of a semiconductor wafer, in accordance with the present invention.

FIG. 6 illustrates a process flow 600 suitable for implementation by the system 100 of the present invention. In one aspect, it is recognized that data processing steps of the process flow 600 may be carried out via a pre-programmed algorithm executed by one or more processors of computing system 116. While the following description is presented in the context of system 100, it is recognized herein that the particular structural aspects of system 100 do not represent limitations and should be interpreted as illustrative only.

In step 602, a three-dimensional design of experiment (DOE) for a plurality of semiconductor wafers may be generated. In step 604, a spectrum may be acquired from the thin films of each of the wafers across a selected spectral range. In step 606, a set of optical dispersion data may be generated by extracting the real component (n) and the imaginary component (k) of the complex index of refraction across the selected spectral range for each of the acquired spectrum utilizing a regression process applied to a selected dispersion model. In step 608, one or more systematic features of the set of optical dispersion data may be identified. It is noted herein that steps 602-608 of process flow 600 are similar to the steps 202-208 of process flow 200. As such, the description of steps 202-208 should be interpreted to extend to the steps 602-608 of process flow 600.

In step 610, a two-dimensional look-up model may be generated by utilizing the identified one or more systematic features of the set of optical dispersion data and the generated set of optical dispersion data. In this regard, the variation of the n- and k- dispersion data as a function of increasing nitrogen content and increasing hafnium content may be utilized to construct a two-dimensional look up model.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages.

The form described is merely explanatory, and it is the intention of the following claims to encompass and include such changes.

What is claimed:

1. A method comprising:
generating, with one or more processors, a three-dimensional design of experiment (DOE) for a plurality of wafers, a first dimension of the DOE being a relative amount of a first component of a thin film, a second dimension of the DOE being a relative amount of a second component of the thin film, a third dimension of the DOE being a thickness of the thin film;
acquiring, with an ellipsometer, a spectrum for each of the wafers across a selected spectral range;
generating, with the one or more processors, a series of optical dispersion data by extracting a real component (n) of a complex index of refraction and an imaginary component (k) of the complex index of refraction across the selected spectral range for each of the acquired spectrum utilizing a regression process applied to a selected dispersion model;
identifying, with the one or more processors, one or more systematic trends within the series of optical dispersion data acquired from the plurality of wafers as a function of at least one of the first dimension, the second dimension or the third dimension, wherein the one or more systematic trends in the series of optical dispersion data are characterized by at least one of a rotation parameter; and
generating, with the one or more processors, a multi-component Bruggeman effective medium approximation (BEMA) model utilizing the identified one or more systematic trends characterized by at least one of the rotation parameter within the series of optical dispersion data acquired from the plurality of wafers as a function of at least one of the first dimension, the second dimension or the third dimension and the generated series of optical dispersion data acquired from the plurality of wafers.

2. The method of claim 1, wherein the first component of the thin film comprises:
nitrogen.

3. The method of claim 1, wherein the second component of the thin film comprises:
hafnium.

4. The method of claim 1, wherein the wafer comprises:
a silicon wafer.

5. The method of claim 1, wherein the thin film comprises:
a thin film including at least one of hafnium, silicon, nitrogen and oxygen.

6. The method of claim 1, wherein the acquiring, with an ellipsometer, a spectrum for each of the wafers across a selected spectral range comprises:
acquiring a spectrum for each of the wafers across a selected spectral range utilizing a spectroscopic ellipsometer (SE).

7. The method of claim 1, wherein the acquiring, with an ellipsometer, a spectrum for each of the wafers across a selected spectral range comprises:
acquiring a spectrum for each of the wafers across a selected spectral range of 150 to 850 nm.

8. The method of claim 1, wherein the regression process comprises:
a least squares regression process.

9. The method of claim 1, wherein the selected dispersion model comprises:
at least one of a Tauc-Lorentz model, a sum model having two Tauc-Lorentz components, a Cody-Lorentz model, or a harmonic oscillator model.

10. The method of claim 1, wherein the identifying, with the one or more processors, one or more systematic trends within the set of optical dispersion data comprises:
determining, with the one or more processors, a behavior of the set of optical dispersion data as a function of the relative amount of the first component of the thin film.

11. The method of claim 1, wherein the identifying, with the one or more processors, one or more systematic trends within the set of optical dispersion data comprises:
determining, with the one or more processors, a behavior of the set of optical dispersion data as a function of the relative amount of the second component of the thin film.

12. The method of claim 1, wherein the multi-component Bruggeman effective medium approximation (BEMA) model comprises:
at least one of a four-component BEMA model, a five-component BEMA model, an eight-component BEMA model or a nine-component BEMA model.

13. A method comprising:
generating, with one or more processors, a three-dimensional design of experiment (DOE) for a plurality of wafers, a first dimension of the DOE being a relative amount of a first component of a thin film, a second dimension of the DOE being a relative amount of a second component of the thin film, a third dimension of the DOE being a thickness of the thin film;
acquiring, with an ellipsometer, a spectrum for each of the wafers across a selected spectral range;
generating, with the one or more processors, a set of optical dispersion data by extracting a real component (n) of a complex index of refraction and an imaginary component (k) of the complex index of refraction across the selected spectral range for each of the acquired spectrum utilizing a regression process applied to a selected dispersion model;
identifying, with the one or more processors, one or more systematic trends within the set of optical dispersion data, wherein the one or more systematic trends in the set of optical dispersion data are characterized by at least one of a rotation parameter or an additional parameter; and
generating, with the one or more processors, a two-dimensional look up model utilizing the identified one or more systematic trends characterized by at least one of the rotation parameter or the additional parameter within the set of optical dispersion data acquired from the plurality of wafers as a function of at least one of the first dimension, the second dimension or the third dimension and the generated set of optical dispersion data acquired from the plurality of wafers.

14. The method of claim 13, further comprising:
generating, with the one or more processors, a multi-component Bruggeman effective medium approximation (BEMA) model utilizing the identified one or more systematic trends within the set of optical dispersion data acquired from the plurality of wafers as a function of at least one of the first dimension, the second dimension or the third dimension and the generated set of optical dispersion data acquired from the plurality of wafers.

15. The method of claim 13, wherein the first component of the thin film comprises:
nitrogen.

16. The method of claim 13, wherein the second component of the thin film comprises:
hafnium.

17. The method of claim 13, wherein the wafer comprises:
a silicon wafer.

18. The method of claim 13, wherein the thin film comprises:
a thin film including at least one of hafnium, silicon, nitrogen and oxygen.

19. The method of claim 13, wherein the acquiring, with an ellipsometer, a spectrum for each of the wafers across a selected spectral range comprises:
acquiring a spectrum for each of the wafers across a selected spectral range utilizing a spectroscopic ellipsometer (SE).

20. The method of claim 13, wherein the acquiring, with an ellipsometer, a spectrum for each of the wafers across a selected spectral range comprises:
acquiring, with an ellipsometer, a spectrum for each of the wafers across a selected spectral range of 150 to 850 nm.

21. The method of claim 13, wherein the regression process comprises:
a least squares regression process.

22. The method of claim 13, wherein the selected dispersion model comprises:
at least one of a Tauc-Lorentz model, a sum model having two Tauc-Lorentz components, a Cody-Lorentz model, or a harmonic oscillator model.

23. The method of claim 13, wherein the identifying, with the one or more processors, one or more systematic trends within the set of optical dispersion data comprises:
determining, with the one or more processors, a behavior of the set of optical dispersion data as a function of the relative amount of the first component of the thin film.

24. The method of claim 13, wherein the identifying, with the one or more processors, one or more systematic trends within the set of optical dispersion data comprises:
determining, with the one or more processors, a behavior of the set of optical dispersion data as a function of the relative amount of the second component of the thin film.

25. A system comprising:
an illuminator;
a spectrometer;
one or more computing systems configured to:
generate a three-dimensional design of experiment (DOE) for a plurality of wafers, a first dimension of the DOE being a relative amount of a first component of a thin film, a second dimension of the DOE being a relative amount of a second component of the thin film, a third dimension of the DOE being a thickness of the thin film;
acquire a spectrum for each of the wafers across a selected spectral range from the spectrometer;
generate a set of optical dispersion data by extracting a real component (n) of a complex index of refraction and an imaginary component (k) of the complex index of refraction across the selected spectral range for each of the acquired spectrum utilizing a regression process applied to a selected dispersion model;
identify one or more systematic trends within the set of optical dispersion data acquired from the plurality of wafers as a function of at least one of the first dimension, the second dimension or the third dimension, wherein the one or more systematic trends in the set of optical dispersion data are characterized by at least one of a rotation parameter; and
generate at least one of a two-dimensional look up model or multi-component Bruggeman effective medium approximation (BEMA) model utilizing the identified one or more systematic trends characterized by at least one of the rotation parameter within the set of optical dispersion data acquired from the plurality of wafers as a function of at least one of the first dimension, the second dimension or the third dimension and the generated set of optical dispersion data acquired from the plurality of wafers.

26. The system of claim 25, wherein the first component of the thin film comprises:
nitrogen.

27. The system of claim 25, wherein the second component of the thin film comprises:
hafnium.

28. The system of claim 25, wherein the wafer comprises:
a silicon wafer.

29. The system of claim 25, wherein the thin film comprises:
a thin film including at least one of hafnium, silicon, nitrogen and oxygen.

30. The system of claim 25, wherein the spectrometer comprises:
a spectrometer of a spectroscopic ellipsometer (SE).

31. The system of claim 25, wherein the spectrometer and the illuminator form a portion of a spectroscopic ellipsometer (SE).

32. The system of claim 25, wherein the one or more computing systems is configured to apply a least squares regression process.

33. The system of claim 25, wherein the one or more computing systems is configured to apply at least one of a Tauc-Lorentz model, a sum model having two Tauc-Lorentz components, a Cody-Lorentz model, or a harmonic oscillator model.

* * * * *